United States Patent [19]
Wu et al.

[11] Patent Number: 5,656,274
[45] Date of Patent: Aug. 12, 1997

[54] THROMBOXANE A$_2$ RECEPTOR ANTAGONISM AND ANTIOXIDANT ACTION OF CINNAMOPHILIN AND ITS DERIVATIVES

[75] Inventors: Tian-Shung Wu, Tainan; Che-Ming Teng; Sheu-Meei Yu, both of Taipei, all of Taiwan

[73] Assignee: National Science Council of Taiwan, Taipei, Taiwan

[21] Appl. No.: 394,113

[22] Filed: Feb. 24, 1995

[51] Int. Cl.$^6$ ................................. A01N 65/00
[52] U.S. Cl. ........................ 424/195.1; 424/440
[58] Field of Search ..................... 424/440, 195.1

[56] References Cited

U.S. PATENT DOCUMENTS 4,595,693  6/1986  Biftu et al. ............................ 514/461

OTHER PUBLICATIONS

Han et al., *Chemical Abstracts*, vol. 104(23), 1986, #203866a.

Biftu et al., *Chemical Abstracts*, vol. 90(7), 1979, #54746z.

Heiser et al., *Chemical Abstracts*, vol. 88(19), 1978, #131379x.

Hoffmann–La Roche, *Chemical Abstracts*, vol. 76(23), 1972, #140220r.

Voudrias et al., Chemical Abstracts, vol. 99, 1984, #200266.

Constam et al., Chemical Abstracts, vol. 116, 1992, #17560.

Csiba et al., Chemical Abstracts, vol. 116, 1990, #28169.

Welsh et al., Chemical Abstracts, vol. 112, 1990, #8961.

*Primary Examiner*—D. Gabrielle Phelan
*Attorney, Agent, or Firm*—W. Wayne Liauh

[57] ABSTRACT

The present invention discloses the method of isolation and purification of the bioactive constituents cinnamophilin from *Cinnamomum philippinense* (Merr.), the same as *Machilus acuminatissima* (Hayata). Pharmacological evaluation showed that these compounds possess the activity to inhibit platelet aggregation and to produce relaxing effects of aortic vascular constriction.

4 Claims, 2 Drawing Sheets

THROMBOXANE A₂ RECEPTOR ANTAGONISM AND ANTIOXIDANT ACTION OF CINNAMOPHILIN AND ITS DERIVATIVES

The invention reveals the formula(A) wherein $R_1$ represents H, $C_{1-8}$ alkyl, —OCOR, wherein $R_2$ represents OH, COO—, wherein R represents H, $C_{1-8}$ alkyl.

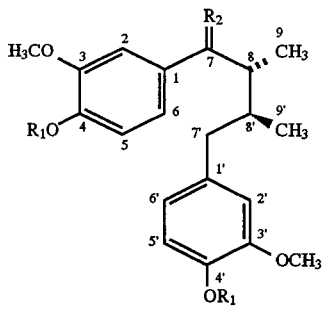

TECHNICAL FIELD OF THE INVENTION

The present invention discloses the isolation and therapeutical application of some novel lignan derivatives. These derivatives have the formula (A) wherein $R_1$ represents H, $C_{1-8}$ alkyl, —OCOR, wherein $R_2$ represents OH, COO—, wherein R represents H, $C_{1-8}$ alkyl.

The discovery of thromboxane $A_2(TXA_2)$ and prostacyclin($PGI_2$) has generated a great deal of interest in these highly potent derivatives of arachidonic acid(AA). $TXA_2$ is the major cyclo-oxygenase product derived from AA in blood platelets. It is an extremely potent platelet aggregator, vasoconstrictor and bronchoconstrictor. $PGI_2$ is produced by vascular endothelium and has potent biological actions opposing those of $TXA_2$. Normally there is a homaeostatic balance maintained between $TXA_2$ and $PGI_2$. However, in some pathological conditions (e.g. thrombosis), the normal balance is upset allowing the detrimental properties of $TXA_2$ to predominate. Thus, drugs that inhibit $TXA_2$ formation or action may have a potential as antithrombotic agents.

Cyclo-oxygenase inhibitors (e.g. aspirin) have been criticized for their alleged capability of suppressing the synthesis not only of $TXA_2$ but also of $PGI_2$, a powerful antiaggregatory and vasodilator substance. The use of the more recently introduced thromboxane(TX) synthase inhibitors has been questioned on the basis of a possible proaggregatory activity of prostaglandin endoperoxides($PGG_2$, $PGH_2$) accumulating after the block of TX synthase. $TXA_2$ receptor antagonists have the advantage of inhibiting the proaggregatory action of both $TXA_2$ and prostaglandin endoperoxides and also of antagonizing the effects of these agonists on smooth muscle cells. However, they do not suppress platelet activation mediated by $TXA_2$-independent agonists (high dose collagen, thrombin).

Drugs with combined TX synthase inhibitory and $TXA_2$ receptor antagonistic properties may overcome several of the shortcomings of the pharmacological classes discussed above. Indeed, while TX synthase inhibition enhances the endogenous synthesis of antiaggregatory prostaglandins ($PGI_2$ and $PGD_2$), $TXA_2$ receptor antagonism prevents accumulated endoperoxides from activating platelets and smooth muscle cells. The summation of these effects may theoretically lead to an increase of adenosine 3',5'-cyclic monophosphate(cyclic AMP) in platelets and smooth muscle cells, a phenomenon associated with strong platelet inhibition and smooth muscle relaxation.

The prior drugs belong to these inhibitors are ridogrel and picotamide. Hoet et al. reported that ridogrel inhibited thromboxane $A_2$ synthetase with an $IC_{50}$ of 5 nM, which is 130 times less than that inhibiting thromboxane receptor, with an $IC_{50}$ of 2 μM (Blood, 75, 646–53, 1990). Ridogrel never simultaneously achieves double actions at the same blood concentration. Gresele et al. reported that picotamide might have therapeutic action at concentration as high as 100 μM, the side effect might become apparant.(Thromb. Haemost. 61, 479–84, 1989). It is therefore important for us to search for new drugs with high efficacy, lower side effect by inhibiting thromboxane synthetase and thromboxane receptor, for the therapy of thrombosis.

When an excessive amount of oxygen free radicals are produced or defense mechanisms are impaired, highly reactive free radicals tend to set off chain reactions. There is now an increasing amount of evidence that oxidative damage is a major contributor to the etiology of degenerative diseases, including aging, brain dysfunction, cancer, AIDS, and cardiovascular diseases.

Lipid peroxidation not only causes alterations in the structure of the membrane but also rises to reactive lipid epoxides, lipid hydroperoxides, lipid alkoxyl and peroxyl radicals, and enals. It is undoubted that transition metals as catalysts, iron or copper, are involved in both initiation and propagation of lipid peroxidation. Free radical-mediated lipid peroxidation may be critically important in two unique pathophysiological events.

In recent years, there has been much evidence linking atherogenesis with free radical-mediated oxidation of low-density lipoprotein(LDL). Oxidatively modified, which is different from native LDL in both surface charge and by the presence of aldehyde-lysine adducts, has been recognized and enhanced uptaken by a scavenger receptor of macrophage, leading to formation of lipid-laden foam cells, one of the first stages of atherogenesis. According to in vivo and in vitro studies, classical chainbreaking antioxidants are suggested to be beneficial for protecting LDL against lipid peroxidation, therefore, preventing occurrence of atherogenetic events.

BHA(t-Butylhydroxyanisole) or BHT(t-butylhydroxytoluene) are artifical anti-oxidants as food additive; however, their safety are considerable. On the other hand, α-tocopherol is used as a natural anti-oxidant. α-Tocopherol is unfavourably used for food additive, because it has some defects such as its a fat-soluable vitamin; its cost is quite high; its antioxidative action on fatty oils is lower than BHA(t-butylhydroxyanisole) or BHT (t-butylhydroxy toluene); so it can not substitute artifical antioxidant. It is therefore important for seaching artifical antioxidants with lower cost, and water soluable.

Medicinal plants have been widely used as traditional remedies in oriental countries for hundreds of years. Recently, in a large scale screening test, we have found that cinnamophilin, a new lignan(FIG. 1), isolated from *Cinnamomum philippinense*, possessed both TX synthase inhibitory and $TXA_2$ receptor antagonizing properties. Lu et al. reported the isolation of other alkaloids (not cinnamophilin) from the root of this plant(Yakagaku Zasshi 87,1278, 1967). In this study, the pharmacological effect of cinnamophilin was determined in vitro in human platelets, rat isolated aorta and guinea-pig isolated trachea and in vivo in mice and guinea-pigs.

DETAILED DESCRIPTION

The present invention discloses the efficient methods of isolation and purification of the bioactive constituents from the root parts of the medicinal plant, *Cinnamomum philippinense*(Merr.) Chung(same as, *Machilus acuminatissima*(Hayata)Kanehira) and a novel series of cinnamophilin derivatives.

The present invention also discloses the isolation and therapeutical application of some novel lignan derivatives. These derivatives have the formula(A) wherein $R_1$ represents H, $C_{1-8}$ alkyl, —OCOR, wherein $R_2$ represents OH, COO—, wherein R represents H, $C_{1-8}$ alkyl. Cinnamophilin is one of the novel bioactive constituents which structure as follow.

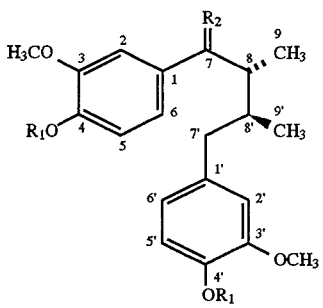

The methods of isolation might be performed using polar organic solvent such as methanol, ethanol and acetone. Solvent of the extract from root parts of *Cinnamomum philippinense* was evaporated and the residue was suspended in water, and extracted with chloroform or other non-polar organic solvents. Bioassay was performed by using this chloroform layer in platelet aggregation test, rat aortic contraction, and guinea-pig tracheal contraction. Purified bioactive components were obtained through silica gel column, then afforded cinnamophilin (1), two known lignan compounds as (+)-guaiacin(3), meso-dihydroguaiaretic acid (2) and an aromatic acid as vallinic acid. The bioactivity of meso-dihydroguaiaretic acid(2) has not been observed.

The invention also discloses the preparation methods of these compounds as shown in FIG. 1. As A route, dissolving cinnamophilin(1) with ether or other preferred solvents, added known alkylation agent to afford alkoxyl derivative of II. As B route, cinnamophilin(1) with preferred acidity solvents processed ester reaction to afford ester derivative of III. Via C route, with preferred reduction agent processed alkoxyl group or ketone group of cinnamophilin(1) and derivative of II to afford derivative of V.

Said organic solvents are alcohols, ketones, chloroform. The methylation reaction was processed with solvent as ether and diazomethane, or acetylation with solvent as pyridine and acetoacetate that were by the prior method. The reduction was processed with solvent as methanol and $NaBH_4$.

Compounds II–V wherein $R_1$ represents H, $C_{1-8}$ alkyl, —OCOR, wherein $R_2$ represents OH, COO—, wherein R represents H, $C_{1-8}$ alkyl. Preferred substituted alkyl group is 8 carbon number, optical alkyl group is 6 carbon number. Structures of these compounds were elucidated on the basis of their IR, UV, $^1$H-NMR, $^{13}$C-NMR, Mass spectra as well as the elemental analytical data. The pharmacological evaluation showed that these compounds possess the activity to inhibit the platelet aggregation, antioxidative, and relaxing effect of aortic contraction, and tracheal contraction.

Inhibiting activity on platelet aggregation

A. Preparation of aggregation inducing agent

1. Collagen(bovine tendon) in 15 mM aqueous acetic acid was homogenized at 4° C. to form a well dispersed suspension in 1 mg/ml and stocked at –70° C. Before using, it was thawed and well homogenized.

2. PAF was dissolved in $CCl_4$ and stocked at 20° C. Before using, it was diluted with deionized water.

3. Adenosine(ADP)and sodium arachidonate(AA) were dissolved in deionized water for use.

B. Preparation of platelets

A suspension of platelets was prepared according to the reported method. EDTA(100 mM) and the blood obtained from rabbit's ear vein were mixed in the ratio of 1:4, and immediately centrifuged(120×g) at room temperature for 10 minutes. Platelet-rich plasma was subjected to further centrifuge (500×g) for another 10 minutes. After the plasma was removed, the platelets in the lower layer were suspended in the Tyrode solution containing EDTA(2 mM) and bovine serum albumin(3.5 mg/ml), and subjected to centrifuge (500×g) again for 10 minutes. The platelets obtained were suspended in a Tyrode solution containing no EDTA, and was adjusted to about $4.5 \times 10^8$ cells/ml by a cell counter. 1 mM of calcium ion($Ca^{2+}$) was added to the suspension. 30 minutes after the addition, the experiment was conducted. The composition of Tyrode(mM): NaCl(136.9), KCl(2.7), $NaH_2PO_4$ (0.4), $NaHCO_3$(11.9), glucose(11.1).

C. Platelet aggregation and ATP release reaction test

The method reported by Born (J.Physiol. 168,178, 1963) was used to determine the platelet aggregation by a Lumi-aggregometer (Model 1020, Payton, Canada). Platelet suspension(0.4 ml) was added into a small glass tube coated with silicone, and stirred at 900 rpm with a small magnetic stirrer. Unless otherwise specified, the antagonist was added 1 minute before the inducing agent, and all the reactions were carried out at 37° C. The aggregation was calculated by following formula:

aggregation(%)=(light absorption before adding inducing agent–light absorption after adding inducing agent)/ (light absorption before adding inducing agent –light absorption of Tyrode solution)×100%

Relaxing effect of aortic vascular contraction, and tracheal contraction.

A. Rat Aortic Contraction

Wistar rats of either sex weighing 250 g to 300 g were killed by a blow to the head. The thoracic aorta was isolated and excess fat and connective tissue were removed. Vessels were cut into rings of about 5 mm in length and mounted in organ baths containing 5 ml Krebs solution of the following composition (mM): NaCl(118.4), KCl(4.7), CaCl(1.9), $MgSO_4$(1.2), $KH_2PO_4$(1.2), $NaHCO_3$(25.0) and glucose (11.7). The tissue bath solution was maintained at 37° C. and gassed with 95% $O_2$:5% $CO_2$ mixture. Two stainless steel hooks were inserted into the aortic lumen, one was fixed while the other was connected to a transducer. Aortae were equilibrated in the medium for 90 min with three changes of Krebs solution and maintained under an optimal tension of 1 g before specific experimental protocols were initiated.

Contraction was recorded isometrically via a force-displacement transducer connected to a Grass polygraph. Aortae were allowed to preincubate for 15 minutes with cinnamophilin before generating the cumulative concentration-response curve with each agonist for 15–30 min at 3 min intervals. Results are expressed as a percentage of the maximal control response for each agonist.

B. Guinea-pig tracheal contraction

Tracheae from guinea-pigs were dissected out, transferred to a dish containing Krebs solution and cut transversely between the segments of cartilage. Several of these, usually about 5, were tied together so as to form a chain, which was then mounted in Krebs solution at 37° C., gassed with 95%

$O_2$ plus 5% $CO_2$. One end of the chain was attached to a fixed pin in the bath and the other to a transducer connected to a Grass polygraph. Resting tension of each tissue was set at 1 g, Tracheae were allowed to equilibrate for at least 1 hr and washed-periodically.

Cumulative concentration-response curves were obtained by application of various concentrations of spasmogens for 15–18 min at 3 minutes intervals. Tracheal rings were pre-incubated with cinnamophilin for 15 min, then various concentrations of spasmogens were added for 15–18 min at 3 min intervals. Results were expressed as percentage of the maximal control response for each agonist.

C. Antioxidation Assay

Peroxidation of rabbit brain vesicular membrane lipids was assayed as previously described. Rabbit brain was homogenized in 25 mM tris-(hydroxymethy)aminomethane HCl containing 0.15M potassium chloride, pH 7.5 (10% wt/vol), and centrifuged at low speed(1.000×g for 15 minutes). The test agent(dissoved in 5 µl dimethyl sulfoxide) was added to the supernatant fraction (0.5 ml), which was then incubated with 220 µM adenosine diphosphate and 2 µM ferric chloride at 37° C. for 1 hr. The control supernatant was not incubated. The reaction was terminated by adding 0.4 mL of thio-barbituric acid-reactive substance reagent (0.02% trichloroacetic acid and 0.8% thio-barbituric acid) and boiled for 1.5 minutes. The sample was acidified with 2.3N HCl(0.5 mL), extracted with 1-butanol(1 mL), and centrifuged at 3,000 g for 5 minutes.

The absorbency of the butanol phase was determined at 532 nm in a spectrophotometer and the amount of malondialdehyde present was determined by linear regression analysis of standard curve.

In some experiments, the cinnamophilin was found potentially to inhibit the platelet aggregation induced by arachidonic acid(AA), ADP, collagen, U-46619, A-23187. A potential inhibition was observed in U-46619 induced platelet aggregation. Cinnamophilin also found to inhibit second phase aggregation of human platelet-rich plasma caused by ADP(adenosine diphosphate) and adrenaline (Table. 1). The compounds were found to inhibit markedly the rabbit platelet aggregation which was induced by 100 µM AA, 1 µM U-46619, 10 µg/ml collagen, 0.1 U/ml thrombin, 20 µM ADP, 2 ng/ml PAF, 0.5% DMSO as control(Table 2). 0.03–10 µM of cinnamophilin was found to inhibit markedly the $TXA_2$ formation caused by AA, and simultaneously increase $PGE_2$ and cAMP levels(Table 3). Cinnamophilin was found also to inhibit the rat aortic contraction induced by U-46619 at 7.3±0.2 pA2 comparing to 0.5% DMSO as control(Table 4). It also was found to inhibit the guinea-pig tracheal contraction which was induced by U-46619 at 5.2±0.1 pA2(Table 5). Cinnamophilin also inhibited the phasic contractions induced by noradrenaline and high potassium(80 mM) (Table 6).

By antioxidation assay cinnamophilin was found to be a potential antioxidation capable comparing to 0.5% DMSO as control. The absorbency of the butanol phase was determined at 500 nm in a spectrophotometer shown as Table 7 and FIG. 2, 20 µM of cinnamophilin was found the antioxidation capable lower than α-tocopherol at the same concetration, but a potential antioxidation capable comparing to 0.5% DMSO as control. 40 µM cinnamophilin possesses potential inhibitory effect on fatty oil peroxidation.

The novel cinnamophilin derivatives of the invention that possess the pharmacological activity of inhibiting the platelet aggregation and vasorelaxing effect of aortic contraction, may accordingly be administered to treat varied cardiovascular diseases of living animal body. The novel cinnamophilin derivatives have bioactivity of inhibiting the tracheal contraction may accordingly be administered to treat varied asthma diseases of living animal body. The living animal body including a human and warm animal.

The pharmaceutical ,preparations according to the invention which contains compounds of the formula(A) for enteral or parenteral administration which contain the pharmaceutically active ingredient by itself or together with a pharmaceutically acceptable carrier material. Suitable carriers for oral dosage form are, in particular, filers, suchs as sugars, for example lactose, sucrose, mannitol, and furthermore binders, such as starch mucilage using, for example, wheat, rice or potato starch, and/or, if desired, distegrating or adjuncts. Those carriers for parenteral dosage form are, in particular, aqueous solutions and furthermore lipophilic solvents or vehicles, such as fatty oils, and/or, if desired, viscosity-increasing substance, for example, sodium carboxymethylcellulose, sorbitol.

The novel cinnamophilin derivatives of the invention showed that these compounds possess the select thromboxane synthetase inhibitor, simultaneous inhibited the thromboxane receptor, so that possessing two bioactivity, as inhibited platelet activity and vasorelaxing effect. The dosage of the compounds according to this invention is 10–300 mg/day, preferably 20–100 mg/day, when administered to patients, e.g. humans, as drug.

The novel cinnamophilin derivatives of the invention that possess the activity of anti-oxidation. Cinnamophilin derivatives the same as α-tocopherol were natural antioxidant, it could be instead of α-tocopherol as the modern food additive. The food preparations which contains compounds of the formula(A), the active ingredient with a foods additive and acceptable carrier material. Suitable carriers are flavours, adjuncts, sweetener, spices.

Figure 1:
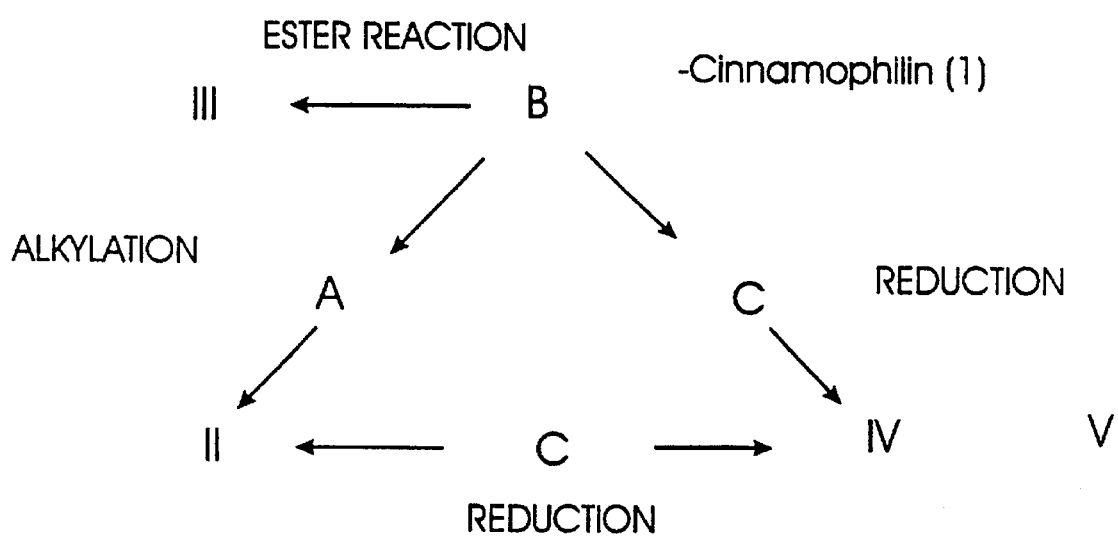
FIG. 1 Preparation procedure
Figure 2:
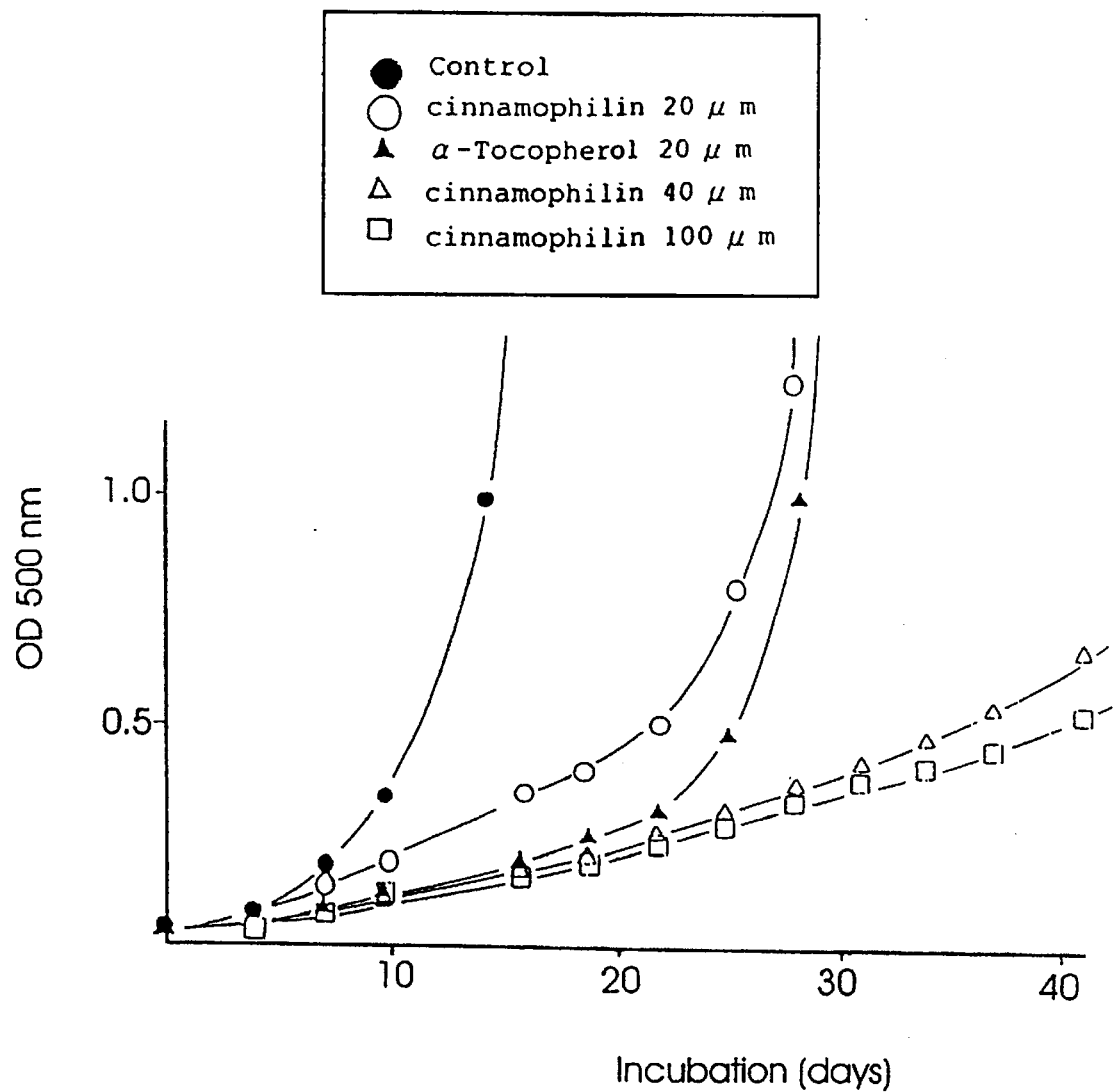
FIG. 2 Antioxidative action

Tab.1 Aggregation test of human pletelet-rich plasma

Tab.2 Effects of compounds 1, 4, 5, 7 and 2 on the aggregation of rabbit platelet suspension Tab.3 Effects of cinnamophilin on the thromboxane $B_2$, $PGE_2$ and cAMP formations caused by arachidonic acid (AA)

Tab. 4 Effect of cinnamophilin on the rat aortic contraction caused by U-46619

Tab.5 Effect of cinnamophilin on contraction of guinea-pig trachea caused by U-46619 (% of maximal contraction)

Tab.6 Effects of compounds 1, 4, 5, 7 and 2 on the rat aortic contraction caused by norepinephrine(3 µm) and high potassium (KCl,80 mM), 0.1% DMSO as control, N: not determined Tab.7 Antioxidation of cinnamophilin and vitamin E (Absorbance at 500 nm, using FeSCN method)

Tab.8 Physical data of cinnamophilin derivatives

EXAMPLE 1

An amount of 1 Kg of the roots of the *Cinnamomum philippinense*(Merr.)Chungna was extracted 5 times volumn of methanol. This residue was suspended in 5% HCl in $CHCl_3$, heaving the alkaloids then subjected to column chromatography through a 70–230 mesh silica gel to give cinnamophilin(1).

mp: 89°–91° C.

$[\alpha]_D$:+60.1° (c, 1.1, CHCl₃) EtOH

UVλmax nm (log ε): 230, 278, 305,

EMS (m/z, %):344 (M⁺,3), 180 (100), 164(86), 151(44), 137(35), 123(19), 108(12), 94(14), 77(14), 65(14), 55(10), 52(9).

Anal. Calcd. for $C_{20}H_{24}O_5$: C, 69.75; H, 7.02.

Found: C, 69.70; H, 7.06.

KBr

IR (νmax cm⁻¹): 3550, 1660, 1595, 1510 cm⁻¹.

¹³C-NMR (CDCl₃,δ): 11.4(q, C-9'), 15.2(q, C-9), 37.7(d, C-7'), 41.3(t, C-8'), 42.7(d, C-8), 42.7(d, C-8), 55.8(q, 3-OMe), 55.9(q, 3'-OMe), 110.4(d, C-2), 111.6(d, C-5'), 113.7(d, C-6'), 114.1(d, C-6), 121.9(d, C-2'), 123.2(d, C-5), 129.4(s, C-1), 132.5 (s, C-1'), 144.0(s, C-4'), 146.4(s, C-3'), 146.7(s, C-3), 150.2(s, C-4), 202.8(s, C-7),

EXAMPLE 2

Cinnamophilin(1) (200 g) was dissolved in ether solution added with $CH_2N_2$ at room temperature overnight. Evaporated the solvent under reduced pressure, then subjected to column chromatography through a 70–230 mesh silica gel to give dimethylcinnamophilin(4).

EMS (m/z, %): 372 (M+), 194,178 (100), 165, 163, 151.

KBr

IR ($ν_{max}$ cm⁻¹): 1660, 1585, 1510 cm⁻¹.

¹H-NMR (CDCl₃, δ) 0.86(3H, d, J=6.7 Hz, H-9), 1.40 (3H, d, J=6.7 Hz, H-9'), 2.25(1H, m, J=6.7 Hz, H-8'), 2.46(1H, dd, 6.8 Hz, 13.4 Hz, H-7), 2.60(1H, d, J=7.6 Hz, 13.4 H-7'), 3.35(1H, m, H-8), 3.85(3H, s, OMe), 3.67(6H, s, OMe ×2), 3.92(3H, s, OMe), 6.78(1H, d, J=8.4 Hz, H-6), 7.26(1H, dd, J=2.0 Hz, 8.4 Hz, H-5'),

¹³C-NMR (CDCl₃, δ): 11.1(q), 15.0(q), 30.6(d), 37.3(d), 41.0(t), 42.4(d), 55.5(q), 55.6(t ×3), 109.6(d), 110.3(d), 110.8(d), 112.1(d), 121.0(d), 122.4(d), 129.5(s), 133.0(s), 147.1(s), 148.6(s), 148.8(s), 152.7(s), 202.4(s),

EXAMPLE 3

Cinnamophilin(1) (200 g) was dissolved in pyridine solution added with equal volume $AC_2O$ standing overnight. Poured in ice water, then evaporated the solvent under reduced pressure, subjected to column chromatography through a 70–230 mesh silica gel to give diethylcinnamophilin (5).

EMS (m/z, % ):428 (M⁺), 386, 222, 206, 180, 164 (100), 151, 137, 43.

KBr

IR (νmax cm⁻¹): 1750, 1670, 1595, 1500 cm⁻¹.

¹H-NMR (CDCl₃,δ): 0.87(3H, d, J=6.7 Hz, H-9'), 1.15 (3H, d, J=6.7 Hz, H-9), 2.26(1H, m, H-8'), 2.31 (3H, s, OAc), 2.32 (3H, s, OAC), 2.51 (1H, dd, J=6.8 Hz, 13.8 Hz, H-7'), 3.36 (1H, m, H-8), 3.36(1H, dd, J=8.4 Hz, 13.8 Hz, H-7'), 3.77(3H, s, OMe), 3.82(3H, s, OMe), 6.75(1H, d, J=1.8 Hz, H-2'), 6.75(1H, dd, J=8.4 Hz, 1.8 Hz, 6.95(1H, d, J=8.4 Hz, H-6'), 7.03(1H, d, J=8.2 Hz, H-6), 7.15(1H, dd, J=1.8 Hz, 8.2 Hz, H-5), 7.47(1H, d, J=8.2 Hz),

¹³C-NMR (CDCl₃, δ) 10.5(q), 15.9(q), 20.3(q ×2), 37.0 (d), 41.1(t), 42.5(d), 55.5(q), 55.6(q), 111.5(d), 112.9(d), 121.1(d), 122.2(d), 122.4(d), 135.0(s), 137.9(s), 139.3(s), 143.3(s), 150.7(s), 151.1(s), 168.1(s), 168.7(s), 202.3(s).

EXAMPLE 4

Diethylcinnamophilin (5) (100 g) was dissolved in methanol(20 ml) solution added NaBH₄(150 mg) reaction 5 hrs. Evaporated the solvent under reduced pressure, subjected to column chromatography through a 70–230 mesh silica gel to give diacetylcinnamophilinol (6) and cinnamophilinol(7).

diacetylcinnamophilinol(6)

$[\alpha]_D$: −40.3° (c, 1.0, CHCl₃)

EMS (m/z, % ): 430 (M⁺), 388, 206, 194, 180, 164, 153 (100), 137, 93, 43.

¹H-NMR (CDCl₃, δ): 0.62(3H, d, J=7 Hz, H-9'), 0.87(3H, d, 7 Hz, H-9), 1.60~2.60(4H, m, H-8, 7', 8') 2.24(6H, s, OAc ×2), 3.75(6H, s, OMe ×2), 4.32(1H, d, J=9 Hz, H-7), 6.60~6.90 (6H, m, H-2, 2', 5, 5', 6, 6').

cinnamophilinol(7).

mp: 144°–146° C.

EMS (m/z, % ): 328 (M⁺ −H₂O,100), 271(33), 255(35), 241(65), 204(19), 189(19).

KBr

IR ($ν_{max}$ cm⁻¹): 3425, 1610, 1515 cm⁻¹.

¹H-NMR (CDCl₃,δ): 0.85(3H, d, J=6.2 Hz, H-9), 1.07 (3H, d, J=6.0 Hz, H-9'), 1.58(2H, m, H-8, 8'), 2.59(1H, dd, J=10.6 Hz, 15.8 Hz, H-7'), 2.74(1H, dd, J=4.6 Hz, 15.8 Hz, H-7'), 3.37(1H, br, J=10.1 Hz, H-7), 3.82(3H, s, OMe), 3.85(3H, s, OMe), 5.40(2H, br, OH ×2), 6.25(1H, br, s, H-2'), 6.53(2H, br, s, H-5', 6'), 6.55(1H, d, J=1.8 Hz, H-2), 6.63(1H, dd, J=1.8 Hz, 8.2 Hz, H-6), 6.83(1H, d, J=8.0 Hz, H-5),

¹³C-NMR (CDCl₃ +DMSO-d₆,δ): 17.1(q), 19.9(q), 35.4 (d), 38.8(t), 42.4(d), 52.8(d), 55.6(q), 55.8(q), 110.8(d), 112.5(d), 115.0(d), 116.3(d), 122.0(d), 127.4(s), 132.9(s), 138.0(s), 144.0(s), 144.5(s), 145.5(s), 147.4(s),

EXAMPLE 5

A typical tablet which may be prepared by conventional tabletting techniques contains

| | |
|---|---|
| active compound | 40 mg |
| lactose | 30 mg |
| starch | 8 mg |
| mag. stearate | 10 mg |
| corn starch | 12 mg |

TABLE 1

Aggregation test of human pletelet- rich plasma

| Induce | IC₅₀ (µM) |
|---|---|
| Arachidonic acid(AA) | 5.0 ± 0.4 |
| Collagen | 5.6 ± 0.6 |
| U-46619 | 3.0 ± 0.4 |
| A-23187 | >30 |
| ADP(adenosine diphosphate) | |
| First Phrase | >30 |
| Second Phrase | 6.0 ± 0.6 |
| Adrenaline | |
| First Phrase | >30 |
| Second Phrase | 7.6 ± 0.9 |

AA(800 µM), Collagen(µg/ml),U-46619(1 µM), A-23187(5 µM), ADP(5 µM), Adrenaline (10 µM).

TABLE 2

Effects of 1, 4, 5, 7, and 2 on the aggregation
of washed rabbit platelets induced by AA, PAF, collagen, μ-46619, ADP and thrombin.

| Induce | control | conc (μM) | Aggregation (%) 1 | 4 | 5 | 7 | 2 |
|---|---|---|---|---|---|---|---|
| AA | 92.1 ± 1.3 | 5 | 83.8 ± 4.6* | | | | 76.0 ± 7.8* |
| | | 10 | 79.0 ± 6.3** | | | | 5.9 ± 5.3*** |
| | | 20 | 42.4 ± 3.0** | 87.8 ± 3.3 | 86.3 ± 4.6 | 86.3 ± 1.0* | 0.0 ± 0.0*** |
| | | 50 | 3.8 ± 3.5*** | 75.8 ± 10.6 | 57.8 ± 2.8*** | 75.5 ± 6.2** | — |
| | | 100 | — | 37.7 ± 1.6*** | 0.0 ± 0.0*** | 10.4 ± 9.0*** | — |
| | | 200 | — | 0.0 ± 0.0*** | — | 0.0 ± 0.0*** | — |
| collagen | 93.6 ± 1.0 | 50 | 87.0 ± 1.6** | 86.2 ± 4.7* | 93.4 ± 1.2* | 89.7 ± 3.4 | 79.7 ± 4.7** |
| | | 100 | 44.7 ± 10.0*** | 80.3 ± 3.6** | 80.6 ± 4.7*** | 75.5 ± 2.4** | 16.4 ± 4.4*** |
| | | 200 | 0.0 ± 0.0*** | 7.5 ± 6.4*** | 8.4 ± 7.3*** | 0.0 ± 0.0*** | 0.0 ± 0.0*** |
| U-46619 | 89.4 ± 1.2 | 200 | 22.1 ± 2.4*** | 86.5 ± 1.7 | 88.4 ± 4.3 | 90.4 ± 1.4 | 88.6 ± 3.2 |
| PAF | 91.7 ± 2.0 | 300 | 83.5 ± 8.0 | 0.0 ± 0.0*** | 45.2 ± 9.2*** | 79.7 ± 6.6** | 91.7 ± 2.0 |
| ADP | 81.6 ± 3.0 | 300 | 75.6 ± 9.2 | 30.7 ± 13.0*** | 60.7 ± 12.0*** | 77.3 ± 4.0 | 67.9 ± 8.4* |
| Thrombin | 94.8 ± 2.0 | 300 | 94.6 ± 1.4 | 89.7 ± 3.5 | 94.9 ± 1.0 | 73.2 ± 6.8** | 85.3 ± 6.6 |

Platelets were precincubated with 1a, 1b, 1c, 1e, 2 or DMSO (0.5%, contol) at 37° C. for 3 min, then the inducer was added.
Key Word: Cinnamophilin(1), meso-dihydroguaiaretic acid(2), dimethylcinnamophilin(4), diethylcinnamophilin(5), cinnamophilinol(7
Values are means ±SEM (N = 4–10).
*$P < 0.05$, $P < 0.01$, *$P < 0.001$ as compared with the respective control

TABLE 3

Effects of cinnamophilin on the thromboxane B $PGE_2$ and cAMP formations caused by AA

| conc. (μM) | Thromborane $B_2$ (ng/ml) | Prostaqlandin $E_2$ (ng/ml) | CAMP (pmol/ml) |
|---|---|---|---|
| 0.01 | 371 ± 35 | 40 ± 10 | — |
| 0.03 | 278 ± 25 | 75 ± 15 | — |
| 0.1 | 200 ± 41 | 115 ± 15 | — |
| 0.3 | 128 ± 25 | 155 ± 29 | — |
| 1 | 69 ± 25 | 205 ± 19 | 22 ± 3 |
| 3 | 28 ± 10 | 245 ± 20 | 29 ± 3 |
| 10 | 20 ± 5 | 2665 ± 21 | 35 ± 2 |

TABLE 4

Effect of cinnamophilin on the rat aorti contraction caused by U-46619 (100% of maximal contraction)

| u-46619 (μM) | control | Cinnamophilin (μM) 0.3 | 1 | 3 | 10 |
|---|---|---|---|---|---|
| 0.005 | 8 ± 2 | 0 | — | — | — |
| 0.01 | 26 ± 3 | 8 ± 2 | — | — | — |
| 0.02 | 52 ± 2 | 16 ± 4.9 | 3 | — | — |
| 0.05 | 79 ± 3 | 35 ± 2 | 11 ± 2 | 0 | — |
| 0.1 | 88 ± 1 | 52 ± 3 | 22 ± 3 | 8 ± 3.7 | — |
| 0.2 | 92 ± 2 | 65 ± 4 | 35 ± 3.2 | 15 ± 4.3 | 6 ± 4.3 |
| 0.5 | 95 ± 4 | 79 ± 2 | 53 ± 3.1 | 34 ± 5.6 | 15 ± 3.9 |
| 1 | 96 ± 3 | 85 ± 4 | 65 ± 4 | 50 ± 5.6 | 31 ± 3.8 |
| 2 | 97 ± 2 | 92 ± 4 | 81 ± 4 | 65 ± 5 | 45 ± 3 |
| 5 | 99 ± 3 | | 88 ± 3 | 81 ± 3 | 65 ± 5 |
| 10 | 99 ± 3 | | | 90 ± 3 | 86 ± 4 |

TABLE 5

Effect of cinnamophilin on contraction of guinea-pig trachea caused by U-46619 (100% of maximal contration)

| U-46619 (μM) | control | Cinnamophilin (μM) 10 | 30 | 100 |
|---|---|---|---|---|
| 0.005 | 6 ± 2 | — | — | — |
| 0.01 | 25 ± 5 | 5.7 ± 2 | — | — |
| 0.02 | 40 ± 4.5 | 17.1 ± 4.5 | 3 | — |
| 0.05 | 59 ± 6.2 | 35 ± 5 | 11 ± 3 | 0 |
| 0.1 | 75 ± 5.1 | 52 ± 5 | 22 ± 4 | 5 ± 3 |
| 0.2 | 87 ± 4 | 70 ± 6 | 35 ± 4 | 15 ± 3 |
| 0.5 | 92 ± 5 | 79 ± 4 | 52 ± 5 | 27 ± 4.5 |
| 1 | 96 ± 3 | 85 ± 5 | 67 ± 4 | 41 ± 4 |
| 2 | 100 ± 3 | 90 ± 4 | 80 ± 4.5 | 55 ± 5.7 |
| 5 | 100 ± 4 | 94 ± 4 | 88 ± 5 | 68 ± 5.7 |
| 10 | | | 92 ± 5 | 78 ± 3 |

TABLE 6

Effects of compounds 1, 4, 5, 7 and 2 on the rat aortic contraction caused by norepinephrine (3 μM) and high potassium KCl, 80 nM), 0.1% DMSO as control, N: not determined

| Compound | conc (μM) | norepinephrine (3 μM) contraction (%) Phrase | Tonic | $K^+$ (80 nM) contraction (%) Tonic |
|---|---|---|---|---|
| Control (0.1% DMSO) | | 100 ± 3.1 | 100 ± 7.9 | 100 ± 22.1 |
| 1 | 50 | 65.9 ± 11.3 | 14.6 ± 1.5 | 4.5 ± 3.2 |
| | 10 | 69.3 ± 4.0 | 27.9 ± 0.5 | 5.2 ± 2.3 |
| | 5 | 100.4 ± 9.7 | 77.1 ± 5.7 | N |
| | 3 | 121.8 ± 7.2 | 90.1 ± 5.5 | 36.6 ± 4.7 |
| | 1 | N | N | 60.2 ± 1.5 |
| 4 | 10 | 61.3 ± 2.1 | 48.6 ± 3.3 | 10.5 |
| 5 | 10 | 92.2 ± 13.4 | 64.6 ± 9.1 | 18.4 ± 4.7 |
| 7 | 50 | 95.5 ± 3.2 | 85.3 ± 10.4 | 51.0 ± 4.4 |
| | 10 | 100 | 113.3 ± 7.5 | 66.8 ± 2.2 |
| 2 | 10 | 111.1 ± 6.2 | 78.4 ± 8.8 | 14.8 ± 2.1 |
| | 5 | N | N | 25.7 ± 3.9 |

TABLE 6-continued

Effects of compounds 1, 4, 5, 7 and 2 on the
rat aortic contraction caused by norepinephrine
(3 µM) and high potassium KCl, 80 nM), 0.1% DMSO
as control, N: not determined

| Compound | conc (µM) | norepinephrine (3 µM) contraction (%) Phrase | norepinephrine (3 µM) contraction (%) Tonic | $K^+$ (80 nM) contraction (%) Tonic |
|---|---|---|---|---|
| | 3 | N | N | 36.5 ± 3.2 |
| | 1 | N | N | 74.0 ± 4.1 |

Rat aorta ring were preincubated with lignans or DMSO (0.1% control) at 37° C. for 15 min, then the inducer was added.
Values are means ±SEM (N = 4–10). N: not determined

TABLE 7

Antioxidation of cinnamophilin and vitamin E
(Absorbance at 500 nm, using FeSCN method)

| induce time | control | vitamin E (20 µM) | cinnamophilin 20 µM | cinnamophilin 40 µM |
|---|---|---|---|---|
| 0 | 0.047 | 0.026 | 0.045 | 0.037 |
| 4 | 0.084 | 0.069 | 0.076 | 0.056 |
| 7 | 0.201 | 0.083 | 0.146 | 0.082 |
| 10 | 0.343 | 0.108 | 0.176 | 0.116 |
| 13 | 0.996 | — | — | — |
| 16 | | 0.176 | 0.346 | 0.156 |
| 19 | | 0.226 | 0.399 | 0.204 |
| 22 | | 0.297 | 0.508 | 0.256 |
| 25 | | 0.487 | 0.796 | 0.282 |
| 28 | | 1.024 | 1.301 | 0.349 |
| 31 | | | | 0.405 |
| 34 | | | | 0.453 |
| 37 | | | | 0.525 |
| 40 | | | | 0.687 |

TABLE 8

Physical data of cinnamophilin derivatives

| cinnamophilin (1) | dimethyl cinnamophilin (4) | diethyl cinnamophilin (5) |
|---|---|---|
| 11.4(q, C-9'), | 11.1(q), | 10.5(q), |
| 15.2(q, C-9), | 15.0(q), | 15.9(q), |
| 37.7(d, C-7'), | 30.6(d), | 20.3(q X2), |
| 41.3(t, C-8') | 37.3(d), | 37.0(d), |
| 42.7(d, C-8), | 41.0(t), | 41.1(t), |
| 42.7(d, C-8), | 42.4(d), | 42.5(d), |
| 55.8(q, 3-OMe), | 55.5(q), | 55.5(q), |
| 55.9(q, 3'-OMe), | 55.6(t X3), | 55.6(q), |
| 110.4(d, C-2), | 109.6(d), | 111.5(d), |
| 111.6(d, C-5'), | 110.3(d), | 112.9(d), |
| 113.7(d, C-6'), | 110.8(d), | 121.1(d), |
| 114.1(d, C-6), | 112.1(d), | 122.2(d), |
| 121.9(d, C-2'), | 121.0(d), | 122.4(d), |
| 123.2(d, C-5), | 122.4(d), | 135.0(s), |
| 129.4(s, C-1), | 129.5(s), | 137.9(s), |
| 132.5(s, C-1') | 133.0(s), | 139.3(s), |
| 144.0(s, C-4'), | 147.1(s), | 143.3(s), |
| 146.4(s, C-3'), | 148.6(s), | 150.7(s), |
| 146.7(s, C-3), | 148.8(s), | 151.1(s), |
| 150.2(s, C-4), | 152.7(s), | 168.1(s), |
| 202.8(s, C-7), | 202.4(s), | 168.7(s), |
| | | 202.3(s). |

What we claim is:

1. A process for preparing cinnamophilin derivatives as shown in formula(A) below:

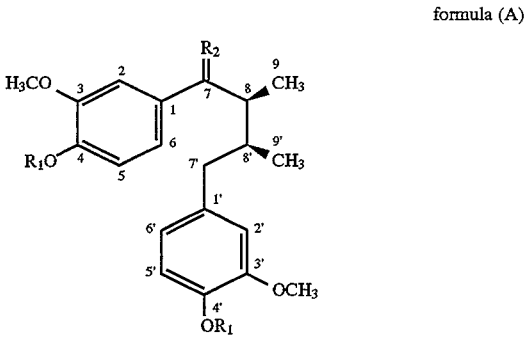

formula (A)

wherein $R_1$ represents H, $C_{1-8}$ alkyl, or —OCOR, wherein R represents H, or $C_{1-8}$ alkyl and wherein $R_2$ represents OH or $COO^-$ and said process comprising the steps of:

(a) extracting root portions of Cinnamomum philippinense (Merrill) Chung with a polar organic solvent to form an extracted solution;

(b) partitioning the extracted solution with a nonpolar solvent to obtain a plurality of liquid layers including a cinnamophilin-derivative-rich layer, which contains largest amounts of cinnamophilin derivatives; and (c) subjecting the cinnamophilin-derivative-rich layer to a column chromatography through silica gel to obtain said cinnamophilin derivatives.

2. The process for preparing cinnamophilin derivatives as shown in formula (A) according to claim 1 wherein said cinnamophilin derivative produced after step (c) is cinnamophilin (1) which is described by the following NMR finger print data:

$^{13}$C-NMR(CDCl$_3$,δ): 11.4 (q, C-9'), 15.2 (q, C-9), 37.7 (d, C-7'), 41.3 (t, C-8'), 42.7 (d, C-8), 55.8 (q, 3-OMe), 55.9 (q, 3'-OMe), 110.4 (d, C-2), 111.6 (d, C-5'), 113.7 (d, C-6'), 114.1 (d, C-6), 121.9 (d, C-2'), 123.2 (d, C-5), 129.4 (s, C-1), 132.5 (s, C-1'), 144.0 (s, C-4'), 146.4 (s, C-3'), 146.7 (s, C-3), 150.2 (s, C-4), 202.8 (s, C-7).

3. The process for preparing cinnamophilin derivatives as shown in formula (A) according to claim 2 which further comprises the step of subjecting such cinnamophilin (1) to an esterification reaction.

4. The process for preparing cinnamophilin derivatives as shown in formula (A) according to claim 2 which further comprises the step of subjecting such cinnamophilin (1) to an alkylation reaction.

* * * * *